United States Patent [19]
Gronauer et al.

[11] Patent Number: 5,945,827
[45] Date of Patent: Aug. 31, 1999

[54] ELECTROMAGNETIC BODY COIL WITH VACUUM CUSHIONS

[75] Inventors: Volker Gronauer, Weissenburg; Arne Reykowski, Pleinfeld, both of Germany; Kamal Vij, Phoenix, Ariz.; Peter Friedl, St. Ulrich am Pillersee, Austria; Helmut Seigerschmidt, Fiegenstall-Hottingen, Germany

[73] Assignees: Gore Enterprise Holdings, Inc., Newark, Del.; W. L. Gore & Associates, GmbH, Germany

[21] Appl. No.: 08/851,730

[22] Filed: May 6, 1997

[30] Foreign Application Priority Data

May 10, 1996 [DE] Germany .................. 196 18 988

[51] Int. Cl.⁶ ........................................ G01V 3/00
[52] U.S. Cl. ............................ 324/318; 600/421
[58] Field of Search ........................ 324/318, 322, 324/314, 319, 300, 309; 600/421, 422

[56] References Cited

U.S. PATENT DOCUMENTS

| | | | |
|---|---|---|---|
| 4,897,604 | 1/1990 | Carlson et al. | 324/318 |
| 5,166,618 | 11/1992 | Jones et al. | 324/318 |
| 5,379,768 | 1/1995 | Smalen | 324/318 |
| 5,617,027 | 4/1997 | Decke | 324/318 |

FOREIGN PATENT DOCUMENTS

| | | |
|---|---|---|
| 39 32 648 | 4/1991 | Germany . |
| 42 21 759 | 4/1993 | Germany . |
| 95/14428 | 6/1995 | WIPO . |

*Primary Examiner*—Louis Arana
*Attorney, Agent, or Firm*—Allan M. Wheatcraft

[57] ABSTRACT

Electromagnetic body coil for magnetic resonance tomographic measurements, whereby the body coil has a three-dimensional coil shape and is assembled from at least two partial coils which are capable of being brought into a state of detachable plug-in connection with one another by means of an electrical plug-in connection arrangement and whereby a first partial coil is located inside a cushion, that serves as a patient resting aid, and the second partial coil is located outside this cushion.

22 Claims, 7 Drawing Sheets

ELECTROMAGNETIC BODY COIL WITH VACUUM CUSHIONS

FIELD OF THE INVENTION

This invention generally relates to an electromagnetic body coil for magnetic resonance tomographic measurements.

BACKGROUND OF THE INVENTION

Body coils for magnetic resonance tomography may be constructed in the form of volumetric coils for accommodating the body part that is to be measured. Volumetric coils are, for example, head coils, neck coils, arm coils, trunk coils and leg coils which accommodate the body part that is to be measured. Such body coils usually have an essentially cylindrical shape.

In order to obtain satisfactory results from examinations with magnetic resonance tomographic devices, the body part that is to be examined should not make any movements relative to the body coil during the measurement process. This is very difficult since the total measurement time in a magnetic resonance tomographic device may be in the range from 30 to 45 minutes. During this long time, the body part that is to be measured has to be held in a movement-free manner in order that one may successfully achieve an acceptable visual image.

In the case of conventional body coils, the electrical coil conductors are embedded in shape-retaining plastic elements. Typically, these plastic elements are relatively hard and are not adapted to the shape of the body part to be measured. This leads, on the one hand, to uncomfortable positioning of the body part that is to be measured and, on the other hand, it makes it difficult for the patient to keep the body part in question free from movement for an adequately long time.

The foregoing illustrates limitations known to exist in present electromagnetic body coils. Thus, it is apparent that it would be advantageous to provide an improved body coil directed to overcoming one or more of the limitations set forth above. Accordingly, a suitable alternative is provided including features more fully disclosed hereinafter.

SUMMARY OF THE INVENTION

The present invention advances the art of electromagnetic body coils beyond which is known to date. The present invention has the objective of improving the resting comfort and immobilization of the patient.

For this purpose, the invention makes available an electromagnetic body coil for magnetic resonance tomographic measurements on body parts of living creatures, whereby this coil has a three-dimensional shape and is assembled from at least two partial coils that are capable of being brought into a state of detachable plug-in connection with one another by means of an electrical plug-type connection arrangement, whereby the first part of the coil is located inside a cushion, which serves as a resting aid, and the second part of the coil is located outside this cushion, which is capable of adaptation to the shape of the body part that is to be measured.

The body coil in accordance with the present invention can be opened by disconnecting the plug-in connection in order to introduce the body part that is to be measured. After placing the body part on the cushion and adapting the cushion to the shape of the body part, it can be closed again by restoring the plug-in connection. Since the body part is supported in conformity with its shape by means of the cushion that has adapted to its shape, one ensures long lasting immobilization of the body part that is to be measured. Higher resting comfort arises for the body part that is to be measured especially when the cushion is filled with a somewhat supple material.

The cushion can be constructed in the form of a vacuum cushion and it can have a gas-tight jacket that is provided with a valve, by means of which the vacuum cushion is capable of being inflated or evacuated, and it is filled to a fraction of its capacity with small, loose particles which are movable in a sand-like manner within the jacket in the case of an adequately inflated jacket and which are held immovably by the jacket in a manner which resembles shrink-foil wrapping in the case of an adequately evacuated jacket. Use is preferably made of particles comprising a somewhat elastically pliable material. Such a vacuum cushion is especially light and readily adaptable to the shape of the body part that is to be measured. One needs only to place the body part on the vacuum cushion, that is in the non-evacuated state, whereby the body part partially sinks into the loose particles similarly to the case with a heap of sand and one then needs only to evacuate the vacuum cushion sufficiently far with the body part placed thereon until the loose particles are held in its shape by the jacket like shrink-foil wrapping. Prior to the measurement of a subsequent patient, one needs only to open the valve, which serves to evacuate the vacuum cushion, in order to be able to adapt the vacuum cushion to the body part of this subsequent patient.

A comprehensive description of such a vacuum cushion which serves as a resting aid is to be found in the subsequently published EP-A-0 713 691 of the applicant.

In order to accommodate the first partial coil, the vacuum cushion is provided with a device for accommodating the partial spool which does not impair the gas-tightness of the jacket. In this way, the jacket can be provided with a gas-tight passageway device by means of which the first partial coil is led through the jacket.

The jacket can be inserted from at least one passageway tube by means of which the part of the first partial coil, which is located within the jacket, is led through the jacket in a manner which does not impair the gas-tightness of the jacket. Alternatively, a textile pouch can be arranged on the jacket, preferably on the underside of the jacket which accommodates the part of the first partial coil which is located within the cushion.

The jacket can be subdivided via at least one gas-permeable separating cross-piece into at least two chambers in the cushion, whereby the chambers are separated from one another and whereby the chambers each accommodate a portion of the small particles. In the case of a non-evacuated vacuum cushion, one can, in this way, prevent the loose particles from sliding, in their entirety or predominantly, to one side of the vacuum cushion.

The exterior of the cushion can be provided with a water-tight functional layer, that is permeable with respect to water vapor, whereby the layer can preferably be microporous stretched PTFE (polytetrafluoroethylene). Alternatively, the jacket itself can consist of a gas-tight and water-tight functional layer which can also be micro-porous, stretched or expanded PTFE which is frequently also designated ePTFE. The use of such a material leads to especially high resting comfort because the wetness which is due to perspiration is dissipated and the unpleasant feeling of wetness does not result in the way in which it can arise in the case of resting on a material that is not permeable to water vapor.

Materials that are suitable for the functional layer comprise micro-porous stretched polytetrafluoroethylene (PTFE), which has already been designated, in the form in which it has been described in U.S. Pat. Nos. 3,953,566 and 4,187,390; stretched PTFE that has been provided with hydrophilic impregnating agents and/or layers in the way in which this has been described in U.S. Pat. No. 4,194,041; polyurethane layers, that are capable of breathing; or elastomers, such as co-polyether esters and their laminates in the way in which they have been described in U.S. Pat. Nos. 4,725,481 and 4,493,870.

The body coil can also be embedded in a shape-retaining plastic element which is assembled from a number of partial coils which correspond to the number of partial plastic elements, whereby one of the partial coils is embedded in each of the partial plastic elements in such a way that plug-in sockets that belong to the plug-in connection arrangement project out of the partial plastic elements.

However, the body coil can also be constructed with a number of self-supporting electrical cable sections which have each been pre-shaped into partial coil form without additional shape-retaining agents, whereby the cable sections are assembled into the body coil by means of electrical connectors. In this way, the cable sections can each contain a plurality of electrical conductors.

Such body coils can be manufactured very inexpensively and require no expensive preparation costs as is the case with the manufacture of injection moldings in order to create a body coil with a special shape or size.

The connectors can be constructed as plug-in connectors. Every connector can comprise a connector housing which has electrical connecting contact elements which are connected to the insulation-free ends of conductors of at least two cable sections and in whose interior and electrical connecting network has been arranged by means of which the connecting contact elements of the connector are connected to one another in a selectable, predetermined electrical connecting pattern. In this way, body coils, which differ in regard to their electromagnetic properties, can be assembled via the use of connectors with connecting networks. For example, both low field measurement devices and high field measurement devices exist. Different magnetic fields are used for different units and/or different measurements. Thus, horizontal magnetic field coils and vertical magnetic field coils exist. Such different body coils have coil conductors that are in different states of electrical connection with one another. And this can be achieved by the use of connectors with suitable connecting networks.

At least part of the connectors can be a plug-in connectors and the connecting contact elements can be constructed in the form of plug-in contact elements which are connected by plugging into the opposite plug-in contact elements at the ends of the cable sections. In this case, one can provide construction kits and one can simply link together the body coils, which are required in each case, from the parts of such a construction kit.

Plug-in connectors that connect cable sections for the plug-in connection of the partial coil bodies can participate in the plug-in connection arrangement.

The cable sections can have at least one plastic component that is capable of being brought into the desired shape by bending and subsequent tempering, whereby the plastic component consists of a material with a memory effect. The cable sections can be constructed as ribbon cable sections and can be assembled with flat conductors.

The body coil and the cushion can be constructed using materials that are capable of being disinfected or, preferably, that are capable of being sterilized. These can be selected from the group comprising polyoxymethylene, polycarbonate and polyurethane. Each of these materials are capable of being treated in an autoclave.

BRIEF DESCRIPTION OF THE DRAWINGS

The foregoing summary, as well as the following detailed description of a preferred embodiment of the invention, will be better understood when read in conjunction with the appended drawings. For purposes of illustrating the invention, there is shown in the drawings an embodiment which is presently preferred. It should be understood, however, that the invention is not limited to the precise arrangement and instrumentality shown. In the drawings.

DETAILED DESCRIPTION OF THE INVENTION

Figure 1:
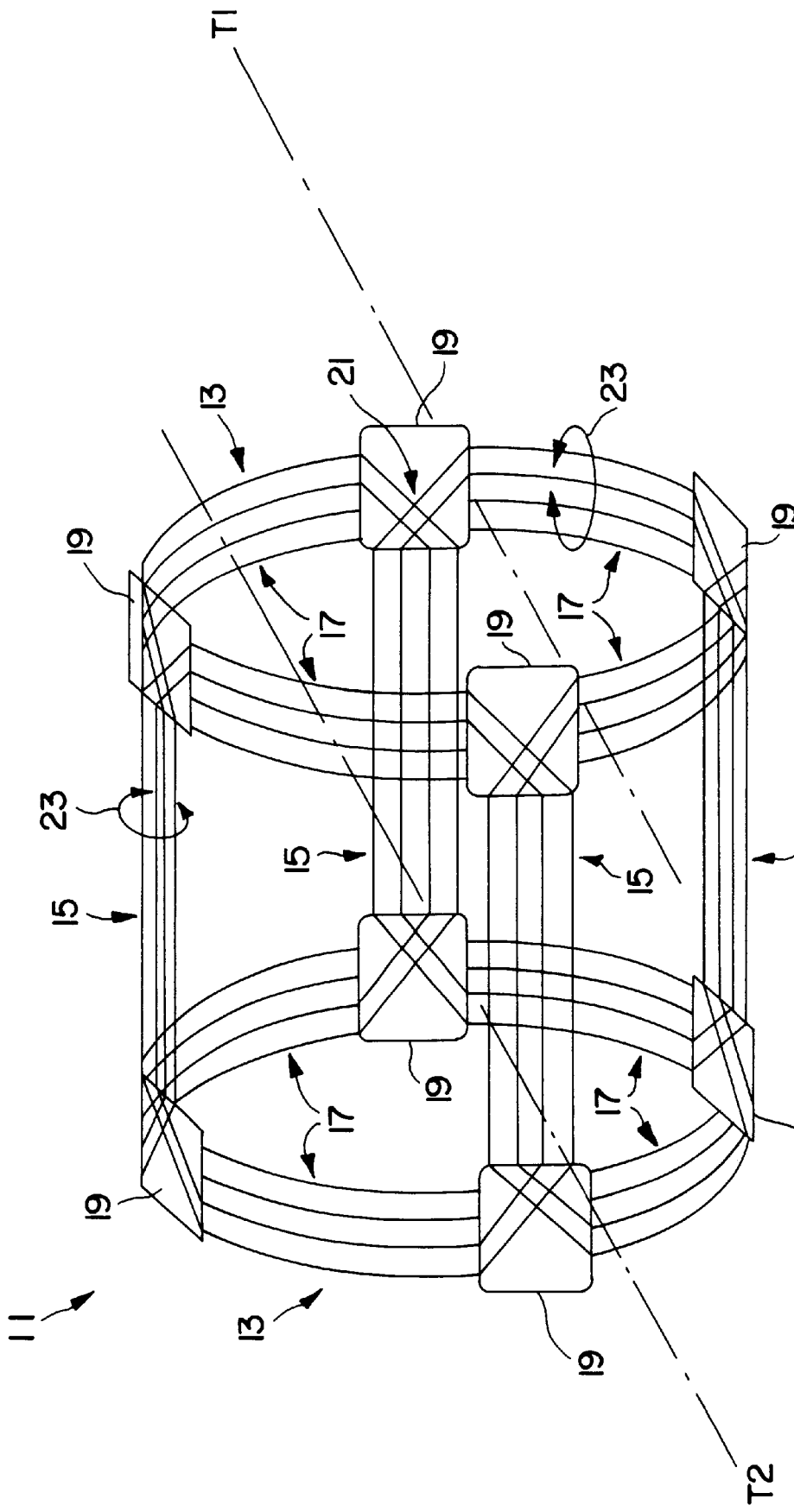
FIG. 1 shows a schematic perspective representation of a cylindrical body coil that is assembled from self-supporting cable sections and connectors.

Referring now to the drawings, wherein similar reference characters designate corresponding parts throughout the several views, FIG. 1 shows a cylindrical body coil 11 in the form of a schematic illustration, which is assembled from several pre-shaped, self-supporting cable sections and several connectors that electrically connect the cable sections to one another. This construction is the subject matter of another simultaneously submitted patent application which has already been mentioned. At each of its axial ends, the body coil 11 comprises a cylindrical cable ring 13 and four linear cable sections 15 which connect the two cable rings together. Each cable ring 13 is assembled from four partially cylindrical cable sections 17. Each longitudinal end of each linear cable section 15 is connected to the ends of two adjacent partially cylindrical cable sections 17 by means of a T-shaped connector 19. At least part of the connectors 19 can be constructed in the form of plug-in connectors in such a way that a detachable plug-in connection exists between the connector 19 in question and the ends of the cable section that are to be connected thereto. Each connector 19 contains an electrical connecting network 21 with which selectable predetermined electrical connections are made between the cable conductors 23 of the participating cable sections.

Two separating lines T1 and T2 are shown in the form of a dashed/dotted representation in FIG. 1. It is thereby intended to indicate that the connection between the connectors 19, that lie on the separating lines T1 and T2 here, and the cable section ends of the lower four partially cylindrical cable sections 17 in FIG. 1 comprises a detachable electrical plug-in connection and is independent of whether all the remaining electrical connections between cable sections and connectors are constructed in the form of a plug-in connection or not. Thus, by detaching the plug-in connections, that lie on the separating lines T1 and T2, one can separate the body coil 11 into a lower or first partial coil 25, which is located below the separating lines T2 and T2 in FIG. 1 and an upper or second partial coil 27, which is located above the separating lines T1 and T2 in FIG. 1 (see FIGS. 2 and 5–7).

However, the possibility also exists, especially when the connectors 19 are not constructed in the form of plug-in connectors to subdivide the two partially cylindrical cable sections 17 at each of the two cable rings 13 into two cable section parts which are connected to one another in a detachable way by means of separating plug-in connectors 29 (FIG. 2), whereby the cable sections are located either on the two sides of a connector 19 that connects them or they are not connected to one another by means of a communal connector 19.

Figure 2:
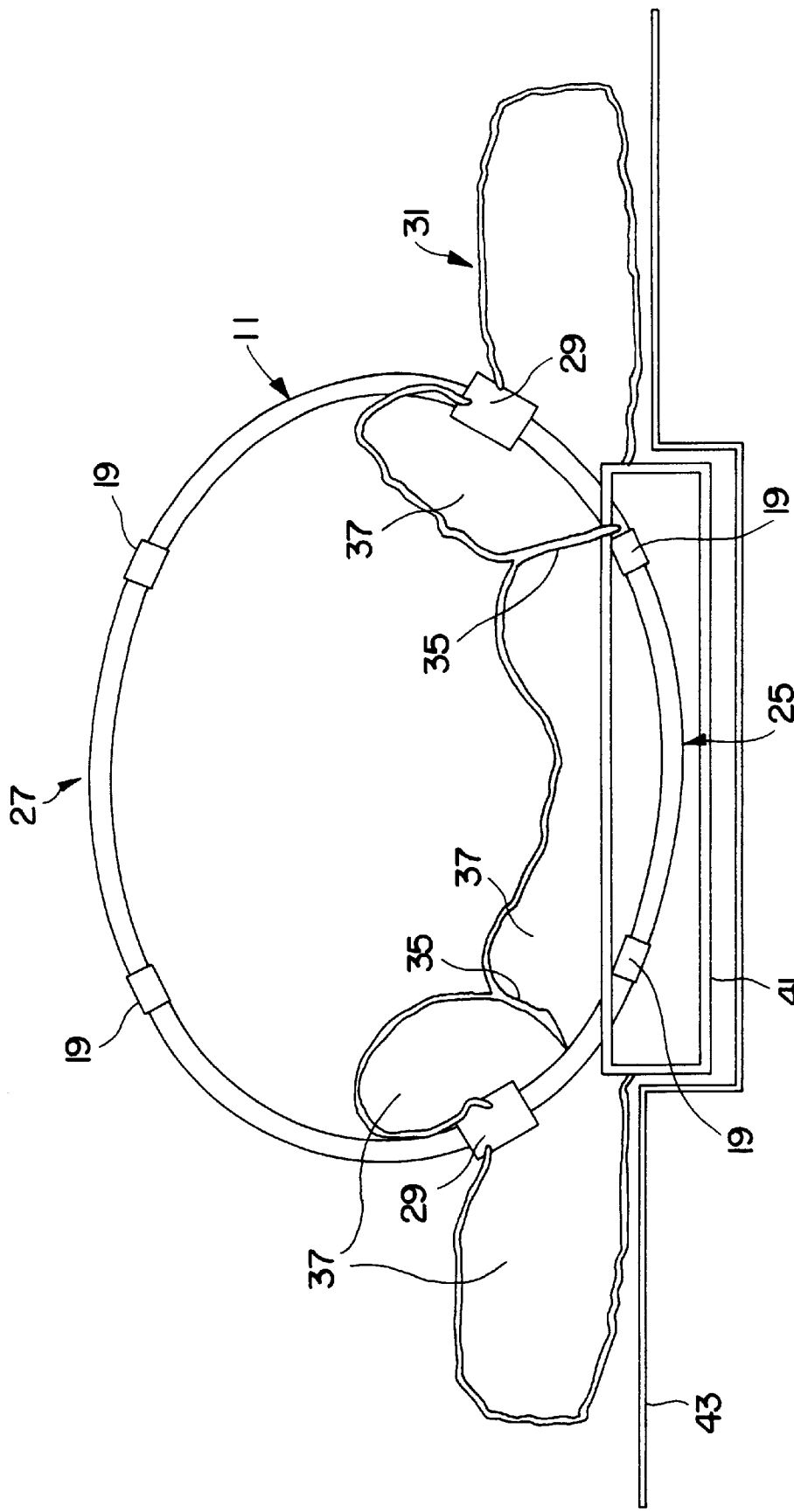
FIG. 2 shows a schematic sectional representation of a body coil, of the type shown in FIG. 1, the body coil being combined with a vacuum cushion with a first partial coil which is located inside the vacuum cushion and a second partial coil which is located outside the vacuum cushion.

FIG. 2 shows an elliptical body coil of the type which is shown in FIG. 1 in the form of a schematic cross-sectional illustration with connectors 19 and separating plug-in connectors 29. The body coil 11, which is shown in FIG. 2, is capable of being separated by means of the separating plug-in connector 29 into the first partial coil 25 and the second partial coil 27. The first partial coil 25 is located within a vacuum cushion 31 that is filled, in the way which has already been described, with small loose particles (not illustrated) and can be adapted, in the way which has already been explained, to the shape of the body part that is to be measured. The vacuum cushion 31 possesses a gas-tight jacket 33 which is subdivided into several chambers 37 by means of separating cross-pieces 35. In this way, one prevents the situation that the loose particles all slide in an undesired manner to one side of the vacuum cushion 31.

The vacuum cushion 31 has a valve 39 (FIGS. 6 through 8) with which the vacuum cushion 31 can be evacuated or inflated. One can now either provide each of the chambers 37 with its own valve 39, or, in a preferred manner, one can make the separating cross-pieces 35 permeable with respect to gas, for example, via perforation, and provide only a single valve 39.

In the case of the embodiment which is shown in FIG. 2, a positioning body 41 is provided below the vacuum cushion 31, whereby the shape of the positioning body is adapted to the surface contours of the patient table 43 that is illustrated only partially in FIG. 2 and this ensures that the construction unit, which comprises the body coil 11 and the vacuum cushion 31, maintains a defined position with respect to the patient table 43. In addition, the jacket 31 is connected in a gas-tight manner to the two separating plug-in connectors 29 and to the positioning body 41.

Figure 3:
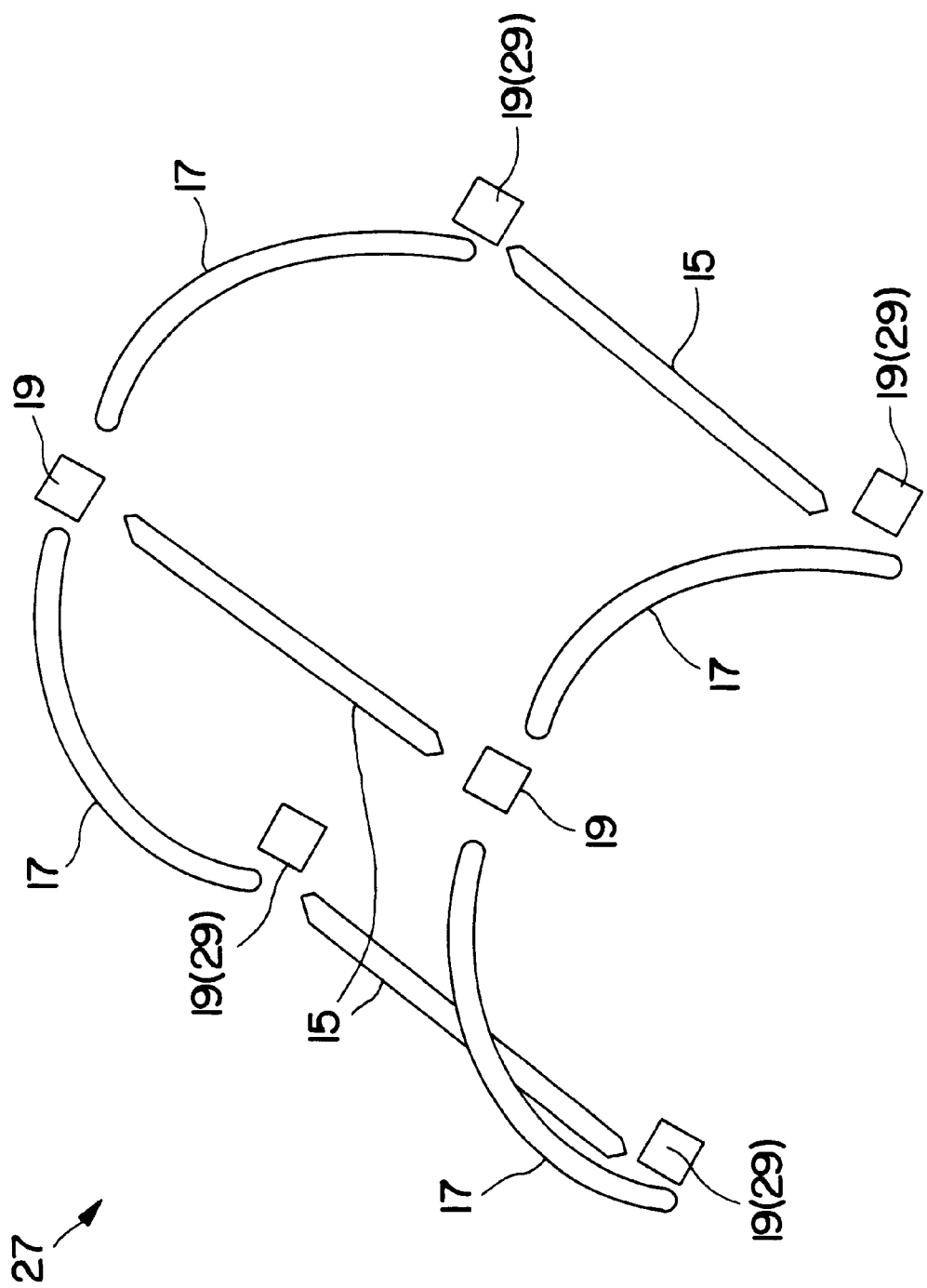
FIG. 3 shows the second partial coil in a schematic exploded view.

In a schematic and partially exploded illustration, FIG. 3 shows the second partial coil 27 which is located outside the vacuum cushion 31. In this way, the connectors, which are shown at the lower ends of the four partially cylindrical cable sections 17 in FIG. 3, are provided both with reference marks 19 and with reference marks 29 in order to indicate that these connectors can be connectors 19 and/or separating plug-in connectors 29 that are provided with connecting networks 21.

Figure 4:
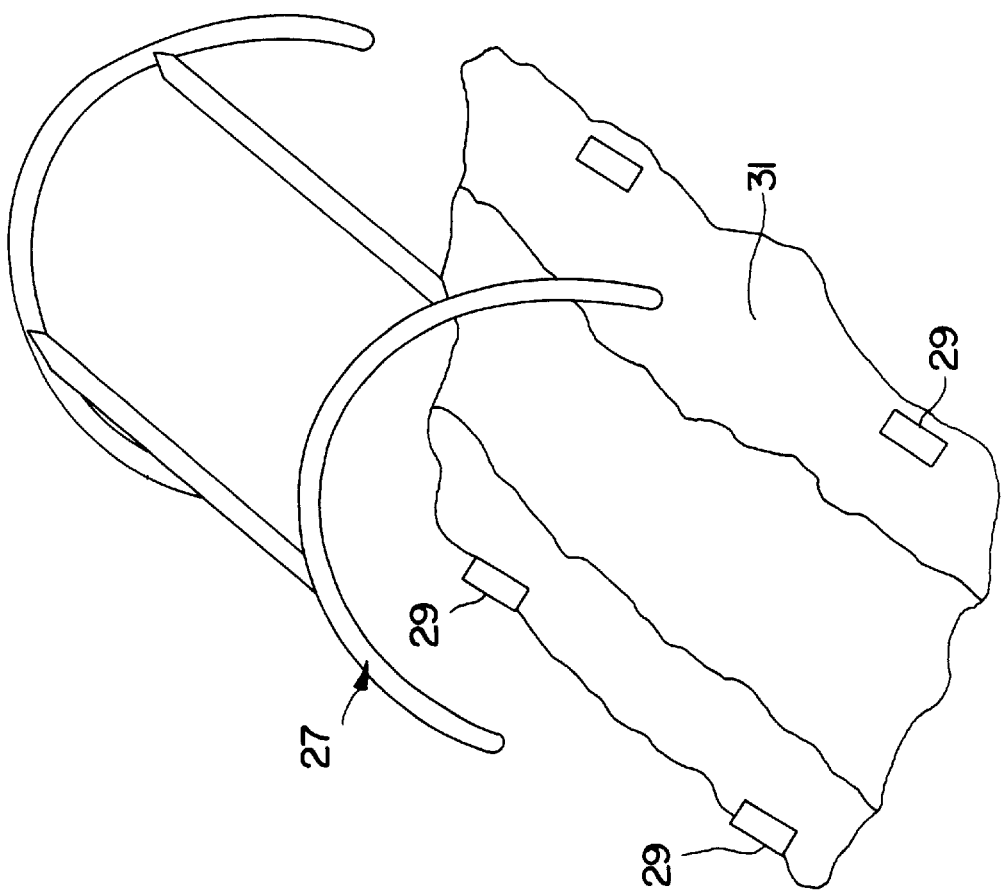
FIG. 4 shows the vacuum cushion and the second partial coil, which is located at a distance above the vacuum cushion, in the form of a schematic illustration.
Figure 5:
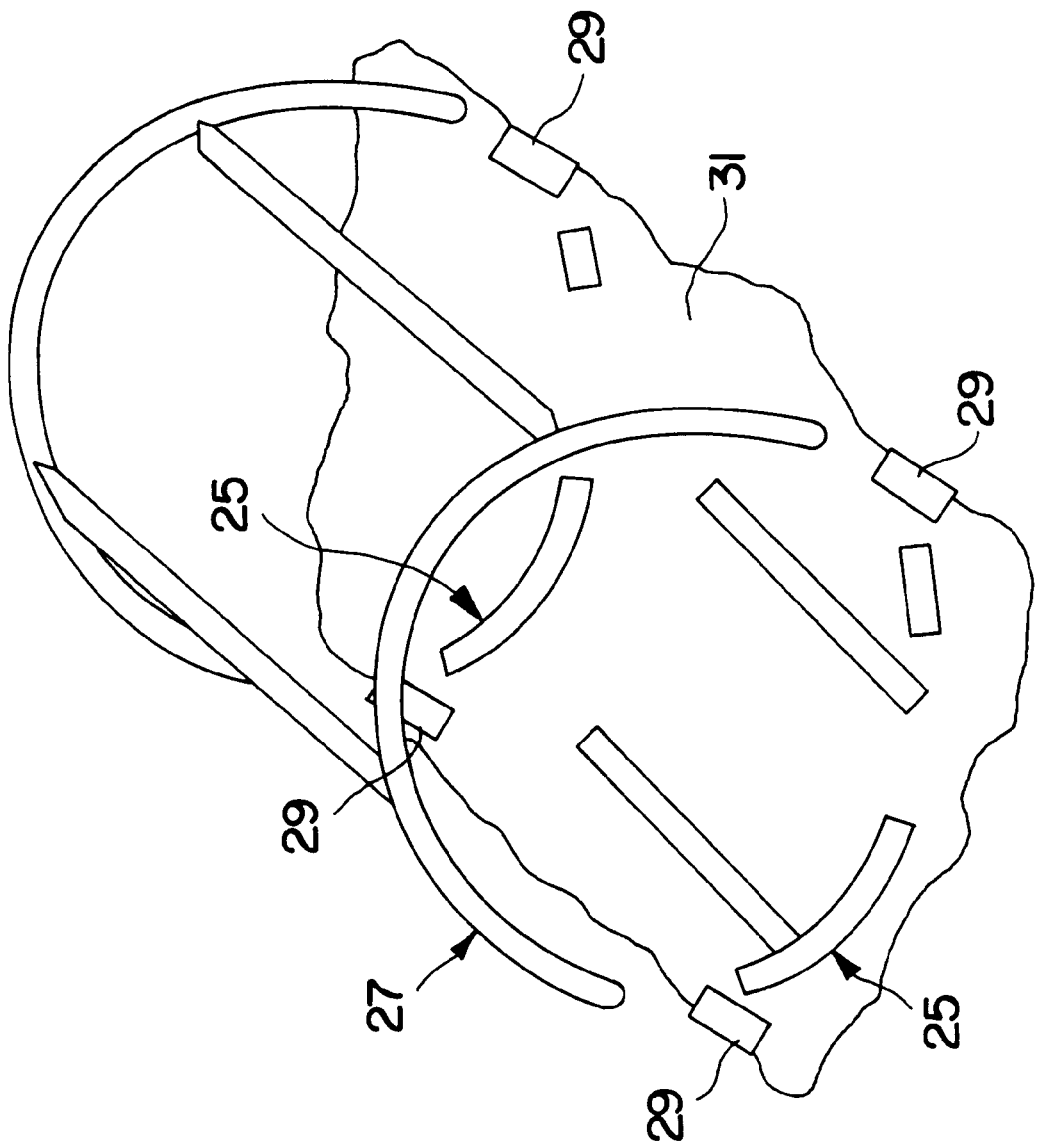
FIG. 5 shows the vacuum cushion with the first partial coil, which is located therein, and the second partial coil, which is located above, in the form of a schematic illustration.

In a schematic illustration, FIG. 4 shows the vacuum cushion 31 with four separating plug-in connectors 29, and, at a distance above, the second partial coil 27 which is located outside the vacuum cushion 31. In a way which is not illustrated, the lower ends of the cylindrical cable sections 17 of the second partial coil 27 in FIG. 4 are capable of being brought into a state of plug-in connection with the separating plug-in connectors 29 which are arranged at the vacuum cushion 31. FIG. 5 illustrates an embodiment similar to FIG. 4, whereby the first partial coil 25, which is located inside the vacuum cushion, is also indicated. The connectors 19, that are provided with the connecting networks 21, are not illustrated in FIGS. 3 through 5.

Figure 6:
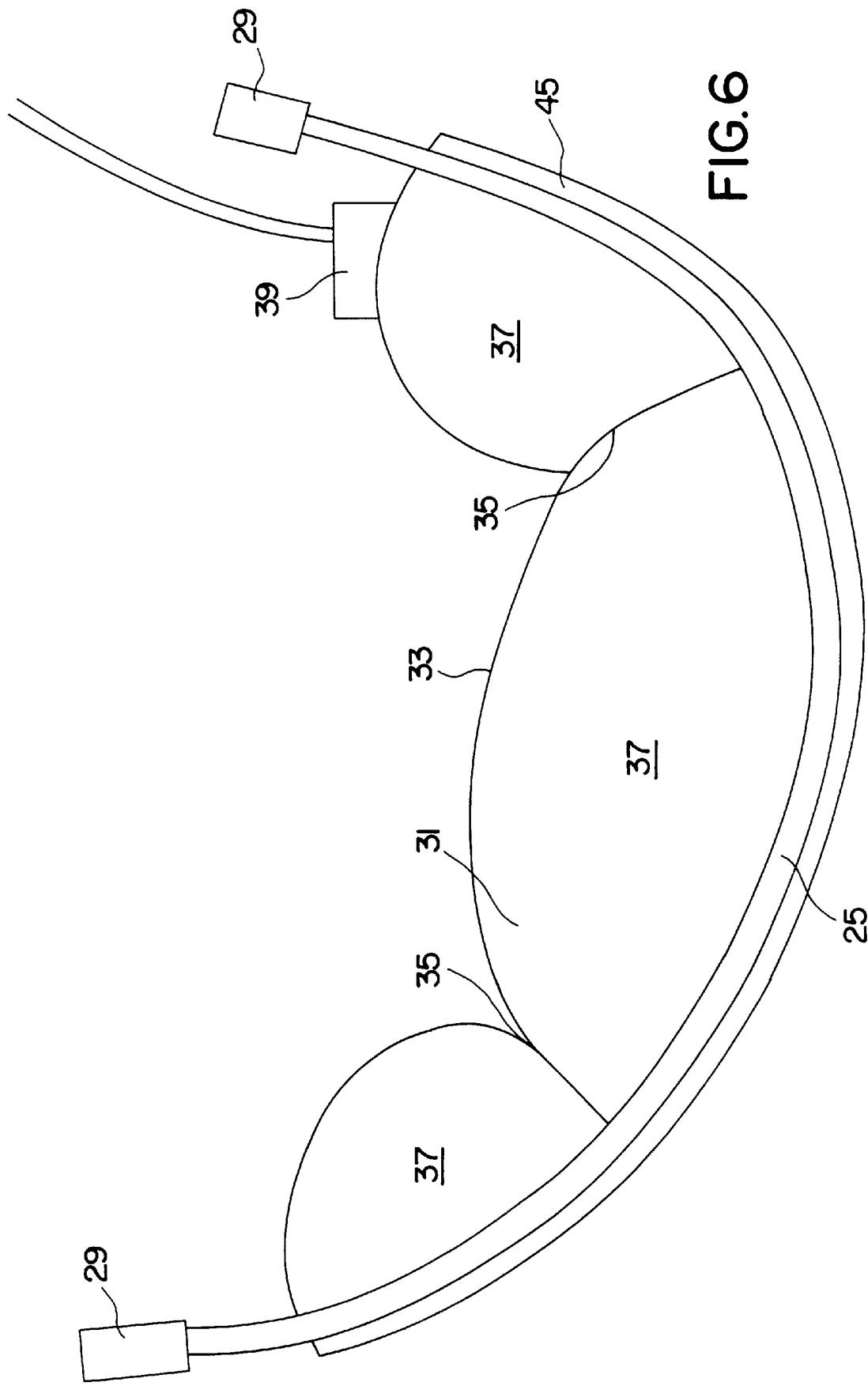
FIGS. 6 and 7 show lateral views of vacuum cushions that are provided with a textile pouch which accommodates the first partial coil.

In a schematic representation, FIG. 6 shows a construction unit comprising the vacuum cushion 31. In FIG. 6, a textile pouch 45 is attached on the underside of the vacuum cushion 31, whereby the first partial coil 25 is located in the textile pouch. In the case of this embodiment, the vacuum cushion 31 does not itself need to be provided with gas-tight passageways for the first partial coil 25. The textile pouch 45 can either be connected permanently to the vacuum cushion 31, for example, by means of gluing, or by means of a detachable connection, for example, by means of hook and loop fasteners. In the case of the form of embodiment that is shown in FIG. 6, the separating plug-in connectors 29 are located outside the textile pouch 45.

Figure 7:
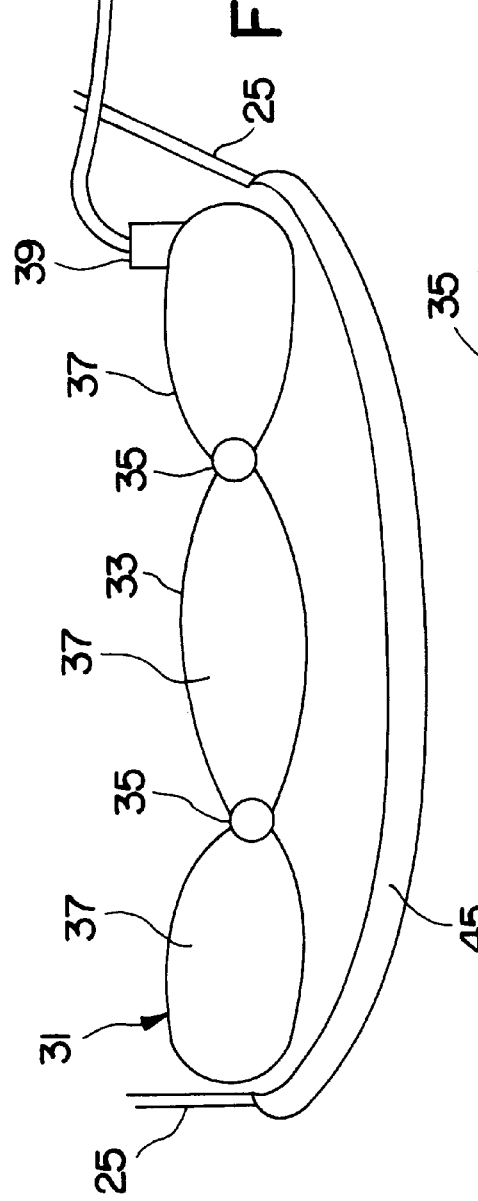
Figure 8:
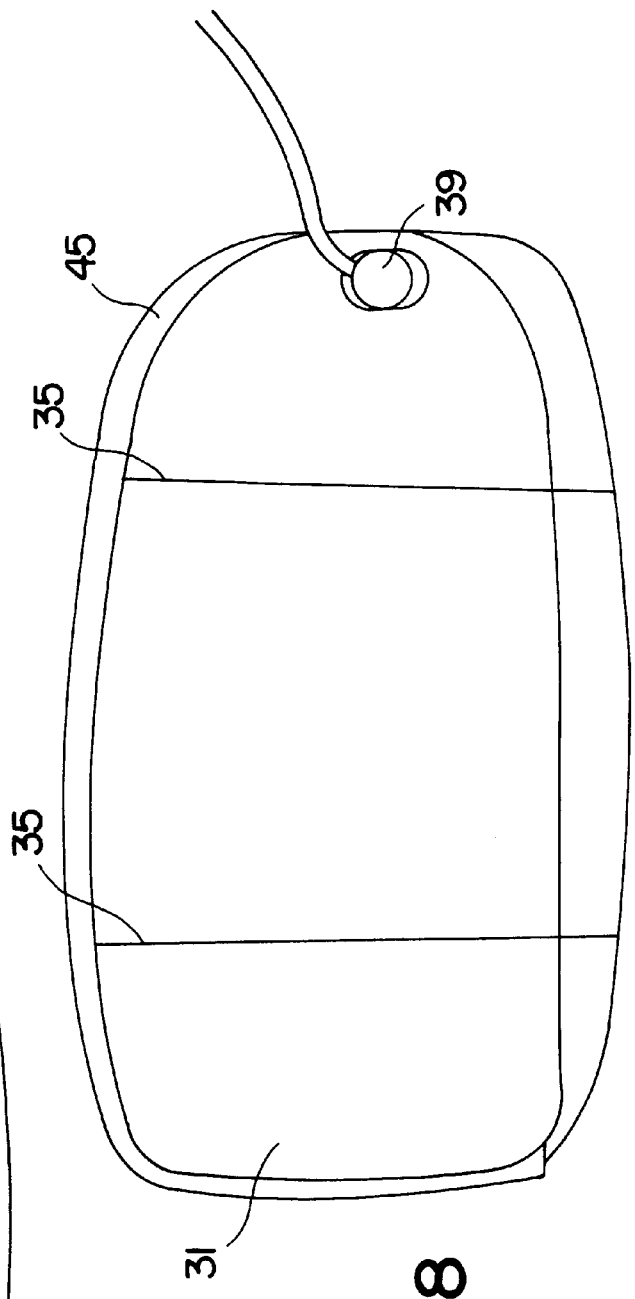
FIG. 8 shows a plan view onto a vacuum cushion of the type which is shown in FIGS. 6 and 7.

A construction unit comprising the vacuum cushion 31, that has been provided with the textile pouch 45, and a first partial coil is also shown in FIGS. 7 and 8, namely in a lateral view or, respectively, a plan view. For example, the two parts of the cable rings 13, which are located on the lower partial coil 25, can be accommodated by pouch regions on the two longitudinal sides of the vacuum cushion 31 that is shown in FIG. 8.

Moving ahead, forms of embodiment have been considered in which the body coil is constructed with self-supporting cable sections. However, the invention is also suitable for body coils which are embedded in a conventional manner in a shape-retaining plastic element. In this case, both the actual coil and the shape-retaining plastic element are subdivided into two partial coils which are capable of being connected together in a detachable manner by means of a plug-in connection which acts electrically and mechanically. In this case, a form of embodiment of the invention is especially suitable in which the first partial coil is accommodated in a textile pouch 45 of a vacuum cushion 31.

Although a few exemplary embodiments of the present invention have been described in detail above, those skilled in the art readily appreciate that many modifications are possible without materially departing from the novel teachings and advantages which are described herein. Accordingly, all such modifications are intended to be included within the scope of the present invention, as defined by the following claims.

Having described the invention, what is claimed is:

1. An electromagnetic body coil for magnetic resonance tomographic measurements of a body, the body coil comprising:
 a three-dimensional coil shape which is assembled from at least two partial coils;
 an electrical plug-in connection for electrically interconnecting said partial coils;
 an evacuable cushion for receiving a first one of the two partial coils therein, said evacuable cushion serving as a resting aid and being adaptable to the shape of the body, the other one of the two partial coils being located outside the evacuable cushion.

2. The body coil as set forth in claim 1, said evacuable cushion having a gas-tight jacket and a valve formed in the jacket for inflating and evacuating the evacuable cushion.

3. The body coil as set forth in claim 2, said cushion further having an insertion tube formed in the jacket, the insertion tube serving as an accommodation device for partial coils, whereby a part of the first partial coil, that is located inside the jacket, is passed through the jacket, in a manner that does not damage the gas-tightness of the jacket by virtue of the insertion tube.

4. The body coil as set forth in claim 2, said jacket having at least one textile pouch that serves as a device for accommodating partial coils, whereby the textile pouch accommodates a part of the first partial coil which is located inside the cushion.

5. The body coil as set forth in claim 2, said jacket being formed by a gas-tight and water-tight material that is permeable to water vapor.

6. The body coil as set forth in claim 5, said jacket being fabricated from stretched micro-porous polytetrafluoroethylene.

7. The body coil as set forth in claim 2, said cushion being filled to a fraction of its capacity with small loose particles that are movable in a sand-like manner inside the jacket in the case of an adequately inflated jacket and that are held immovably as in shrink-foil wrapping in the case of an adequately evacuated jacket, said the cushion being provided with a device for accommodating partial coils, said device not impairing the gas-tightness of the jacket.

8. The body coil as set forth in claim 7, said jacket being subdivided, via at least one gas-permeable separating crosspiece, into at least two cushion chambers that are separated from one another and which each accommodate a portion of the small particles.

9. The body coil as set forth in claim 1, said cushion having an exterior formed by a water-tight material that is permeable to water vapor.

10. The body coil as set forth in claim 1, said body coil being embedded in a shape-retaining plastic element that is assembled from a number of partial coils which correspond to the number of partial plastic elements, one of the partial coils being embedded in each of the partial plastic elements in such a way that plug-in sockets, that are associated with the plug-in connection, project out of the partial plastic elements.

11. The body coil as set forth in claim 1, said body coil having a number of self-supporting electrical cable sections that are pre-shaped in partial coil form without additional shape-retaining agents, the cable sections being assembled by means of electrical connectors.

12. The body coil as set forth in claim 11, each cable section containing one or more electrical conductors.

13. The body coil as set forth in claim 12, said connectors being constructed in the form of plug-in connectors.

14. The body coil as set forth in claim 13, each connector comprising a connector housing having electrical connecting contact elements that are connected to the insulation-free ends of the conductors of at least two cable sections, and an electrical connecting network which is arranged in an interior of the housing by means of the connecting contact elements of the connector which are electrically connected to one another in a selectable predetermined connecting pattern.

15. The body coil as set forth in claim 14, at least part of the connectors being constructed as plug-in connectors and the connecting contact elements being constructed as plug-in contact elements that are in a state of plug-in connection with opposite plug-in contact elements at the ends of the cable sections.

16. The body coil as set forth in claim 14, said plug-in connectors, that connect cable sections, participate in the plug-in connection arrangement for the plug-in connection of the partial coil bodies.

17. The body coil as set forth in claim 11, said cable sections having at least one plastic component that is capable of being brought into the desired shape by means of bending and subsequent tempering.

18. The body coil as set forth in claim 17, said plastic component comprising a material with a memory effect.

19. The body coil as set forth in claim 11, said cable sections being constructed in the form of ribbon cable sections.

20. The body coil as set forth in claim 19, said ribbon cable sections being constructed with flat conductors.

21. The body coil as set forth in claim 1, said body coil and the cushion being constructed with materials that are capable of being disinfected and/or sterilized.

22. The body coil as set forth in claim 21, said materials being selected from the group comprising: polyoxymethylene; polycarbonate; and polyurethane, each material capable of being treated in an autoclave.

* * * * *